(12) United States Patent
Hosoya et al.

(10) Patent No.: US 8,853,192 B2
(45) Date of Patent: Oct. 7, 2014

(54) FAT OR OIL COMPOSITION

(75) Inventors: Naoki Hosoya, Sumida-ku (JP); Shin Koike, Sumida-ku (JP); Takatoshi Murase, Haga-gun (JP)

(73) Assignee: Kao Corporation, Tokyo (JP)

( * ) Notice: Subject to any disclaimer, the term of this patent is extended or adjusted under 35 U.S.C. 154(b) by 460 days.

(21) Appl. No.: 12/376,440

(22) PCT Filed: Aug. 11, 2006

(86) PCT No.: PCT/JP2006/315925
§ 371 (c)(1),
(2), (4) Date: Feb. 5, 2009

(87) PCT Pub. No.: WO2008/018147
PCT Pub. Date: Feb. 14, 2008

(65) Prior Publication Data
US 2010/0267681 A1    Oct. 21, 2010

(51) Int. Cl.
| | |
|---|---|
| A01N 45/00 | (2006.01) |
| A61K 31/56 | (2006.01) |
| A01N 37/00 | (2006.01) |
| A61K 31/20 | (2006.01) |
| A23D 7/00 | (2006.01) |
| A23D 9/00 | (2006.01) |
| C07D 311/00 | (2006.01) |
| A61K 47/00 | (2006.01) |
| A23D 9/007 | (2006.01) |
| A23K 1/16 | (2006.01) |
| C11C 3/02 | (2006.01) |
| C11C 3/06 | (2006.01) |
| A23D 9/013 | (2006.01) |
| A23L 1/30 | (2006.01) |
| C11B 5/00 | (2006.01) |

(52) U.S. Cl.
CPC . *C11C 3/02* (2013.01); *A23D 9/007* (2013.01); *A23K 1/164* (2013.01); *C11C 3/06* (2013.01); *A23D 9/013* (2013.01); *A23L 1/3006* (2013.01); *C11B 5/0035* (2013.01)
USPC ........... 514/171; 426/601; 426/607; 426/611; 426/541; 549/398; 514/558; 514/560; 424/439

(58) Field of Classification Search
USPC .......... 514/171, 558, 560; 426/607, 601, 611, 426/541; 424/439; 549/398
See application file for complete search history.

(56) References Cited

U.S. PATENT DOCUMENTS

| | | | |
|---|---|---|---|
| 6,004,611 A | 12/1999 | Gotoh et al. | |
| 6,025,348 A | 2/2000 | Goto et al. | |
| 6,139,897 A | 10/2000 | Goto et al. | |
| 6,326,050 B1 | 12/2001 | Goto et al. | |
| 6,432,453 B1 | 8/2002 | Krumhar | |
| 6,608,222 B2 | 8/2003 | Bonsignore et al. | |
| 6,762,203 B2 | 7/2004 | Koike et al. | |
| 6,852,758 B2 | 2/2005 | Koike et al. | |
| 7,220,873 B2 | 5/2007 | Yamauchi et al. | |
| 2003/0054082 A1 | 3/2003 | Koike et al. | |
| 2004/0265466 A1 | 12/2004 | Takase et al. | |
| 2005/0165100 A1 | 7/2005 | Kudo et al. | |
| 2005/0214434 A1 | 9/2005 | Yoon et al. | |
| 2006/0057187 A1 | 3/2006 | Eskuchen et al. | |
| 2006/0159824 A1 | 7/2006 | Depierris et al. | |
| 2006/0257454 A1 | 11/2006 | Kudo et al. | |
| 2007/0141220 A1 | 6/2007 | Lee et al. | |
| 2007/0196446 A1 | 8/2007 | Kudo et al. | |
| 2009/0181437 A1 | 7/2009 | Kudo et al. | |

FOREIGN PATENT DOCUMENTS

| | | |
|---|---|---|
| CN | 1906280 A | 1/2007 |
| EP | 0 679 712 A1 | 11/1995 |
| EP | 1 097 708 B1 | 9/2003 |
| JP | 4-300826 | 10/1992 |
| JP | 10-176181 | 6/1998 |
| JP | 2002-194387 | 7/2002 |
| JP | 2002-265374 | 9/2002 |
| JP | 2002 322490 | 11/2002 |
| JP | 2003-113396 | 4/2003 |
| JP | 2003-160794 | 6/2003 |
| JP | 2003-171272 | 6/2003 |
| JP | 2006-75164 | 3/2006 |
| JP | 2006 513307 | 4/2006 |
| JP | 2006 137923 | 6/2006 |
| JP | 2007-512407 | 5/2007 |
| WO | WO 96/06605 | 3/1996 |
| WO | WO 97/46230 | 12/1997 |

(Continued)

OTHER PUBLICATIONS

Yanai et al. (Obesity, 16, 1, 2008, p. 47-51).*
Meguro (Nutrition, 2003, 19, 7/8, 670-675).*
Yeonhwa Park, et al., "Effect of Conjugated Linoleic Acid on Body Composition in Mice", Lipids, vol. 32, No. 8, 1997, pp. 853-858.
Jose A. Arcos, et al., "Rapid enzymatic production of acylglycerols from conjugated linoleic acid and glycerol in a solvent-free system", Biotechnology Letters, vol. 20, No. 6, Jun. 1998, pp. 617-621.
Zheng Guo, et al., "Solvent-Free Enzymatic Synthesis of 1,3-Diconjugated Linoleoyl Glycerol Optimized by Response Surface Methodology", Biotechnol. Prog., vol. 20, No. 2, 2004, pp. 619-622.
Office Action issued Feb. 15, 2011, in Japanese Patent Application No. 2008-528705 with English translation.

(Continued)

*Primary Examiner* — Uma Ramachandran
(74) *Attorney, Agent, or Firm* — Oblon, Spivak, McClelland, Maier & Neustadt, L.L.P.

(57) ABSTRACT

A fat or oil composition containing the following ingredients (A) and (B):
(A) 100 parts by weight of a fat or oil containing 15 wt. % or more of diacylglycerols having, in the constituent fatty acids thereof, an unsaturated fatty acid content of 80 wt. % or more, a conjugated linoleic acid content of from 2 to 92 wt. %, and an ω3 unsaturated fatty acid content of less than 15 wt. %; having a monoacylglycerol content of 5 wt. % or less and a free fatty acid content of 5 wt. % or less; and containing 1,3-diacylglycerol/1,2-diacylglycerol at a weight ratio of from 1 to 5; and
(B) from 0.001 to 2 parts by weight of a tocopherol.

21 Claims, No Drawings

(56) References Cited

FOREIGN PATENT DOCUMENTS

| | | |
|---|---|---|
| WO | WO 99/48378 | 9/1999 |
| WO | WO 00/21379 | 4/2000 |
| WO | WO 00/64854 | 11/2000 |
| WO | WO 01/10989 A1 | 2/2001 |
| WO | WO 02/09691 A1 | 2/2002 |
| WO | WO 02/09693 A1 | 2/2002 |
| WO | WO 02/11552 A2 | 2/2002 |
| WO | WO 2004/096748 A1 | 11/2004 |
| WO | WO 2005/052102 A1 | 6/2005 |

OTHER PUBLICATIONS

Chinese Office Action issued Jun. 5, 2012 in Patent Application No. 200680055598.8 with English Translation.

Official Notice with Information Offer Form issued Jul. 17, 2012 in Japanese Patent Application No. 2008-528705 (with English translation).

Satoshi Fujita, "Food Fat and Oil, and their Applications", First Impression of First Edition, Apr. 5, 2000, 4 pages (with 4 pages of unedited computer-generated English translation).

Chinese Office Action issued Jan. 5, 2013 in Patent Application No. 200680055598.8 with English Translation.

* cited by examiner

FAT OR OIL COMPOSITION

FIELD OF THE INVENTION

The present invention relates to a fat or oil composition having a high content of diacylglycerols containing a conjugated linoleic acid.

BACKGROUND OF THE INVENTION

With the trend toward a healthy lifestyle worldwide, a variety of studies have been made to elucidate the physiological effects of fat or oil. Conjugated linoleic acid, for example, is found to have a therapeutic effect on diabetes or syndrome X as well as an anti-obesity effect and anti-tumor effect (Patent Documents 1 to 5 and Non-patent Document 1). Conjugated linoleic acids having such effects are reported to be applicable to foods (Patent Document 6).

On the other hand, diacylglycerol is found to have an anti-obesity effect and the like (Patent Documents 7 and 8). Moreover, there is a fat or oil known as containing diacylglycerol having a high content of specific fatty acid such as $\omega 3$ fatty acid or linoleic acid (Patent Documents 9 to 11).

Besides, a fat or oil composition obtained by a combination of diacylglycerol and phytosterol is found to have an effective ability to improve the cholesterol level in blood (Patent Document 12).

Conjugated linoleic acid is thought to be not suitable either for easy digestion or as a food, because this acid belongs to a family of free fatty acids and therefore itself has a foreign taste peculiar to free fatty acids. Such a circumstance spurred attempts to open up the spectrum of applications of conjugated linoleic acids by using its ester form (Patent Documents 13 to 18) (Non-patent Documents 2 and 3).

[Patent Document 1] WO 96/06605
[Patent Document 2] WO 97/46230
[Patent Document 3] JP-A-2003-171272
[Patent Document 4] WO 02/009691
[Patent Document 5] WO 02/009693
[Patent Document 6] WO 00/21379
[Patent Document 7] JP-A-04-300826
[Patent Document 8] JP-A-10-176181
[Patent Document 9] WO 01/109899 WO 01/10989
[Patent Document 10] WO 02/11552
[Patent Document 11] EP 0679712A
[Patent Document 12] WO 99/48378
[Patent Document 13] WO 00/64854
[Patent Document 14] WO 04/96748
[Patent Document 15] JP-A-2003-113396
[Patent Document 16] U.S. Pat. No. 6,432,453
[Patent Document 17] U.S. Pat. No. 6,608,222
[Patent Document 18] EP 1097708A
[Non-patent Document 1] Lipids, 32, 853-858 (1997)
[Non-patent Document 2] *Biotechnology Letters*, 20(6), 617-621 (1998)
[Non-patent Document 3] *Biotechnol. Prog.*, 20, 619-622 (2004)

DISCLOSURE OF THE INVENTION

In the present invention, there is thus provided a fat or oil composition containing the following ingredients (A) and (B):

(A) 100 parts by weight of a fat or oil containing 15 wt. % or more of diacylglycerols having, in the constituent fatty acids thereof, an unsaturated fatty acid content of 80 wt. % or more, a conjugated linoleic acid content of from 2 to 92 wt. %, and an $\omega 3$ unsaturated fatty acid content of less than 15 wt. %; having a monoacylglycerol content of 5 wt. % or less and a free fatty acid content of 5 wt. % or less; and containing 1,3-diacylglycerol/1,2-diacylglycerol at a weight ratio of from 1 to 5; and (B) from 0.001 to 2 parts by weight of a tocopherol.

DETAILED DESCRIPTION OF THE INVENTION

In the above-described prior art, even use of a conjugated linoleic acid in the ester form is not satisfactory from the standpoint of flavor and storage stability if a conjugated linoleic acid content is high. A purpose of the present invention is therefore to provide a fat or oil composition which has a high content of diacylglycerols containing a conjugated linoleic acid and has a remarkable anti-obesity effect and excellent stability and moreover, to greatly improve the storage stability of the fat or oil composition.

The present inventors have carried out an investigation. As a result, it has been found that the above-described problems can be overcome by controlling each of the diacylglycerol content in the fat or oil composition, and the conjugated linoleic acid content and tocopherol content in the diacylglycerol to fall within a specific range; and that the fat or oil composition thus obtained has a food-intake suppressive effect, leading to the completion of the present invention. It has also been found that the resulting fat or oil composition has improved storage stability at low temperatures.

The fat or oil composition of the present invention contains a fat or oil (A) as an essential ingredient. The fat or oil (A) contains 15 wt. % (which will hereinafter be called "%", simply) or more of a diacylglycerol (which may hereinafter be called "DAG", simply). It contains preferably from 15 to 95%, more preferably from 20 to 95%, even more preferably from 35 to 95%, even more preferably from 60 to 90%, even more preferably from 70 to 85% from the standpoint of its physiological effect, industrial productivity of the fat or oil, appearance, application to foods, and the like.

In the fat or oil composition of the present invention, unsaturated fatty acids constitute from 80 to 100% of the constituent fatty acids of the diacylglycerols contained in the fat or oil (A). They constitute preferably from 85 to 100%, more preferably from 90 to 98%, even more preferably from 93 to 98% from the standpoint of appearance, physiological effects, and industrial productivity of the fat or oil. These unsaturated fatty acids have preferably from 14 to 24, more preferably from 16 to 22 carbon atoms.

In the fatty acids constituting the diacylglycerols contained in the fat or oil (A) in the fat or oil composition of the present invention, a conjugated linoleic acid (which may hereinafter be called "CLA", simply) content is from 2 to 92%, preferably from 5 to 80%, more preferably from 15 to 70%, even more preferably from 20 to 60%, even more preferably from 25 to 50% from the standpoint of reduction in body fat, suppression of food intake, storage stability, appearance, and intake balance of fatty acids.

Conjugated linoleic acids include 9,11-octadecadienoic acid and 10,12-octadecadienoic acid, positional and geometric isomers thereof, and mixtures thereof. Specific examples include cis-9,trans-11-octadecadienoic acid, trans-9,cis-11-octadecadienoic acid, and trans-10,cis-12-octadecadienoic acid. The conjugated linoleic acid can be produced, for example, by using linoleic acid or a fat or oil having a high linoleic acid content as a raw material and subjecting the raw material to biochemical conjugation with an enzyme derived from ruminants or microorganisms or to chemical conjugation by heating under alkaline conditions.

In the aspect of the present invention, an oleic acid content in the fatty acids constituting the diacylglycerols contained in the fat or oil (A) is preferably from 1 to 65%, more preferably from 2 to 50%, even more preferably from 5 to 40%, even more preferably from 10 to 30% from the standpoint of storage stability, appearance, and intake balance of fatty acids. Moreover, a dioleylglycerol content in the diacylglycerols is preferably less than 45%, more preferably from 0 to 40% from the standpoint of appearance and physiological effects.

An ω3 unsaturated fatty acid content in the fatty acids constituting the diacylglycerols contained in the fat or oil (A) in the fat or oil composition of the present invention is less than 15%. It is preferably from 1 to 10% from the standpoint of stability, appearance, and intake balance of fatty acids. Examples of the ω3 unsaturated fatty acid include α-linolenic acid, eicosapentaenoic acid, and docosahexaenoic acid.

A saturated fatty acid content in the fatty acids constituting the diacylglycerols contained in the fat or oil (A) in the fat or oil composition of the present invention is less than 20%. It is preferably from 0 to 10%, more preferably from 1 to 7%, even more preferably from 2 to 7%, even more preferably from 2 to 6% from the standpoint of appearance, physiological effects and industrial productivity of the fat or oil. The saturated fatty acids have preferably from 14 to 24, more preferably from 16 to 22 carbon atoms, with palmitic acid and stearic acid being even more preferred.

In the aspect of the present invention, the content of trans unsaturated fatty acids, other than conjugated linoleic acids, in the fatty acids constituting the diacylglycerols contained in the fat or oil (A) is preferably form 0 to 3.5%. It is more preferably from 0.1 to 3% from the standpoint of flavor, physiological effects, appearance, storage stability, and industrial productivity of the fat or oil.

In the aspect of the present invention, the content of fatty acids having 12 or less carbon atoms in the fatty acids constituting the diacylglycerols contained in the fat or oil (A) is preferably 5% or less from the standpoint of flavor. It is more preferably from 0 to 2%, even more preferably from 0 to 1%, even more preferably substantially zero. The residual constituent fatty acids have preferably from 14 to 24, more preferably from 16 to 22 carbon atoms.

In the aspect of the present invention, a percentage of 1,3-diacylglycerol (1,3-DAG) in the diacylglycerols (DAG) contained in the fat or oil (A) is preferably 50% or more. It is more preferably from 52 to 100%, even more preferably from 54 to 90%, even more preferably from 56 to 80% from the standpoint of physiological effects, storage stability, industrial productivity of the fat or oil, and flavor. DAG described herein is composed of 1,3-DAG and 1,2-diacylglycerol (1,2-DAG). More precisely, DAG contains 2,3-diacylglycerol, but it is regarded as 1,2-DAG in the present invention.

In the present invention, a 1,3-DAG/1,2-DAG weight ratio in the fat or oil is from 1 to 5. It is preferably from 1.5 to 3.8, more preferably from 2.3 to 5, even more preferably from 2.1 to 3.2 from the standpoint of storage stability at low temperatures, physiological effect, and industrial productivity of the fat or oil.

In the aspect of the present invention, the oil of fat (A) contains from 4.9 to 84.9% of a triacylglycerol (which may hereinafter be called "TAG" simply). The triacylglycerol content is preferably from 4.9 to 64.9%, more preferably from 6.9 to 39.9%, even more preferably from 6.9 to 29.9%, even more preferably from 9.8 to 19.8% from the standpoint of physiological effect, industrial productivity of the fat or oil, and appearance.

In the aspect of the present invention, a conjugated linoleic acid content in the fatty acids constituting the triacylglycerols contained in the fat or oil (A) is preferably 50% or less. It is more preferably from 1 to 35%, even more preferably from 2 to 20%, even more preferably from 5 to 15% from the standpoint of storage stability, physiological effects and industrial productivity of the fat or oil.

In the aspect of the present invention, a weight ratio of the conjugated linoleic acid content in the fatty acids constituting the diacylglycerol contained in the fat or oil (A) to the conjugated linoleic acid content in the fatty acids constituting the triacylglycerols (equation (1)) is preferably from 1 to 10. It is more preferably from 2 to 9, even more preferably from 3 to 8, even more preferably from 4 to 7 from the standpoint of storage stability and physiological effects.

$$\text{(CLA content in DAG)/(CLA content in TAG)} \qquad \text{Equation (1)}$$

In the aspect of the present invention, the oleic acid content in the fatty acids constituting the triacylglycerols contained in the fat or oil (A) is preferably from 15 to 70%. It is more preferably from 20 to 65%, even more preferably from 30 to 60%, even more preferably from 45 to 55% from the standpoint of storage stability, physiological effects and industrial productivity of the fat or oil.

In the aspect of the present invention, unsaturated fatty acids constitute preferably from 70 to 100% of the constituent fatty acids of the triacylglycerols contained in the fat or oil (A). They constitute more preferably from 80 to 100%, even more preferably from 90 to 100%, even more preferably from 93 to 98%, even more preferably from 94 to 98% from the viewpoint of physiological effects and industrial productivity of the fat or oil. The unsaturated fatty acids have preferably from 10 to 24, more preferably from 16 to 22 carbon atoms from the standpoint of physiological effects and industrial productivity of the fat or oil.

In the fat or oil composition of the present invention, the fat or oil (A) contains 5% or less of a monoacylglycerol (which may hereinafter be called "MAG", simply). It contains preferably from 0.1 to 5%, more preferably from 0.1 to 2%, even more preferably from 0.1 to 1.5%, even more preferably from 0.1 to 1.3%, even more preferably from 0.2 to 1% from the standpoint of flavor, appearance, fuming, industrial productivity of the fat or oil, and application to foods.

In the aspect of the present invention, fatty acids constituting the monoacylglycerol contained in the fat or oil (A) are preferably similar to those constituting the diacylglycerol from the standpoint of physiological effect and industrial productivity of the fat or oil.

In the fat or oil composition of the present invention, the content of a free fatty acid and/or salt thereof (which may hereinafter be called "FFA", simply) in the fat or oil (A) is 5% or less. It is preferably from 0 to 3.5%, more preferably from 0 to 2%, even more preferably from 0.01 to 1%, even more preferably from 0.05 to 0.5% from the standpoint of flavor, fuming, comfortable cooking work, and industrial productivity of the fat or oil.

In the aspect of the present invention, the content of unsaturated fatty acids in all the fatty acids constituting the fat or oil (A) is preferably from 80 to 100%. It is more preferably from 85 to 100%, even more preferably from 90 to 100%, even more preferably from 93 to 98% from the standpoint of physiological effects and industrial productivity of the fat or oil.

In the aspect of the present invention, the content of fatty acids having at least four carbon-carbon double bonds in all the fatty acids constituting the fat or oil (A) is preferably from 0 to 40%, more preferably from 0 to 20%, even more preferably from 0 to 10%, even more preferably from 0 to 1% from the standpoint of oxidation stability, comfortable cooking work, physiological effects, coloration, and flavor. The content of substantially zero is even more preferred.

In the aspect of the present invention, the content of trans unsaturated fatty acids in all the fatty acids constituting the fat or oil (A) is preferably from 0 to 4%. It is more preferably from 0.1 to 3.5% from the standpoint of flavor, physiological effects, appearance, and industrial productivity of the fat or oil.

In the present invention, the content of trans unsaturated fatty acids is measured by the AOCS method (American Oil Chem. Soc. Official Method: Celf-96, 2002).

In the aspect of the present invention, the content of the conjugated linoleic acid in all the fatty acids constituting the fat or oil (A) is preferably from 2 to 92%. It is more preferably from 5 to 65%, even more preferably from 10 to 50%, even more preferably from 15 to 30% from the standpoint of physiological effects, storage stability, application to foods, and industrial productivity of the fat or oil.

In an aspect of the present invention, the content of oleic acid in all the fatty acids constituting the fat or oil (A) is preferably from 20 to 65%. It is more preferably from 25 to 60%, even more preferably from 30 to 55%, even more preferably from 35 to 50% from the standpoint of storage stability, application to foods, and industrial productivity of the fat or oil.

In an aspect of the present invention, the content of linolenic acid in all the fatty acids constituting the fat or oil (A) is preferably 15% or less. It is more preferably from 0.1 to 12%, even more preferably from 1 to 10%, even more preferably from 2 to 8% from the standpoint of storage stability, application to foods, industrial productivity of the fat or oil, and physiological effects.

In an aspect of the present invention, either vegetable or animal oils or fats are usable as the raw material of the fat or oil (A). Specific examples of the raw material include rapeseed oil, sunflower oil, corn oil, soybean oil, rice oil, safflower oil, cotton seed oil, and beef tallow. These oils and fats can also be used as sources after adjusting their fatty acid compositions by fractionation, blending, hydrogenation, ester exchange reaction, or the like. Unhydrogenated ones are preferred in view of reducing a trans acid content in all the fatty acids constituting the fat or oil composition.

Moreover, as the fat or oil usable as the raw material of the fat or oil (A), oils or fats which have not been deodorized in advance as well as deodorized oils can be used. In the aspect of the present invention, however, undeodorized oils or fats are preferably used as a portion or all of the raw material in order to reduce the content of trans unsaturated fatty acids other than conjugated linoleic acids and leave phytosterols, phytosterol fatty acid esters, and tocopherols derived from the raw material fat or oil.

In the aspect of the present invention, the fat or oil (A) can be obtained by an esterification reaction among the above-mentioned conjugated linoleic acid, fatty acids derived from the fat or oil, and glycerin, or an ester exchange reaction between the fat or oil containing a conjugated linoleic acid and glycerin, or the like reaction. Excess monoacylglycerols produced by the reaction can be eliminated by molecular distillation or chromatography. Although these reactions can be performed chemically in the presence of an alkali catalyst or the like, it is preferred to conduct them with 1,3-selective lipase or the like under enzymatically mild conditions because of superiority in flavor and the like. It is even more preferred from the standpoint of flavor and storage stability to dilute a diacylglycerol having a high content of a conjugated linoleic acid with a vegetable fat or oil, or carry out an ester exchange reaction between a diacylglycerol having a high content of a conjugated linoleic acid and a vegetable fat or oil.

The fat or oil composition of the present invention is required to contain a tocopherol as ingredient (B). From the standpoint of flavor, oxidation stability, coloration, and the like, a tocopherol (B) content is from 0.001 to 2 parts by weight ("part by weight" or "parts by weight" will hereinafter be called "part" or "parts", simply) based on 100 parts of the fat or oil (A). It is more preferably from 0.005 to 1.5 parts, even more preferably from 0.01 to 1 part, even more preferably from 0.01 to 0.5 part, even more preferably from 0.02 to 0.2 part.

In the aspect of the present invention, α-, β-, γ- or δ-tocopherol or a mixture thereof can be used as the tocopherol (B). From the viewpoint of oxidation stability, use of δ-tocopherol is preferred. In particular, when the fat or oil composition of the present invention is mixed with water or added to a food containing water and the resulting product is stored for a long term or stored in a bright place, use of δ-tocopherol is preferred in order to prevent deterioration of flavor or occurrence of foreign flavor.

Commercially available products of the tocopherol include "E-MIX D" and "E-MIX 80" (each, product of Eisai Co., Ltd.), "MDE-6000" (product of Yashiro Co., Ltd.), and "E-Oil 400" (product of Riken Vitamin Co., Ltd.).

In the aspect of the present invention, in addition to the tocopherol (B), an antioxidant may be added to the fat or oil composition. Any antioxidant may be used insofar as it is ordinarily used for foods. Examples include butylhydroxytoluene (BHT), butylhydroxyanisole (BHA), tertiary butylhydroquinone (TBHQ), catechin, vitamin C or derivatives thereof, phospholipids, and rosemary extract. Of these antioxidants, vitamin C or derivatives thereof, catechin, and rosemary extract are preferred, with a mixture of at least one of them being even more preferred.

As the vitamin C or derivatives thereof, those soluble in the fat or oil (A) are preferred, of which higher fatty acid esters of vitamin C, for example, fatty acid esters having an acyl group with from 12 to 22 carbon atoms are more preferred, L-ascorbyl palmitate and L-ascorbyl stearate are even more preferred, and L-ascorbyl palmitate is even more preferred.

In the aspect of the present invention, the content of the vitamin C or derivative thereof in terms of ascorbic acid is preferably from 0.004 to 0.1 part, more preferably from 0.006 to 0.08 part, even more preferably from 0.008 to 0.06 part based on 100 parts of the fat or oil (A).

In the aspect of the present invention, when the fat or oil composition is mixed with water or is added to a food containing water and the resulting product is stored for a long term or in a bright place, the fat or oil composition is preferably substantially free of a fatty acid ester of L-ascorbic acid as an antioxidant in order to prevent deterioration of a flavor and generation of a foreign flavor.

In the aspect of the present invention, the fat or oil composition preferably contains phytosterols as ingredient (C). The term "phytosterol" as used herein embraces not only a phytosterol which does not form an ester bond between the hydroxyl group thereof and a fatty acid and is in the free form (free phytosterol) but also a derivative of the phytosterol such as an ester.

In the aspect of the present invention, the content of the phytosterols (C) is preferably from 0.05 to 30 parts based on 100 parts of the fat or oil (A). It is more preferably from 0.3 to 20 parts, even more preferably from 1 to 10 parts, even more preferably from 2 to 8 parts, even more preferably from 2.5 to 4.7 parts from the standpoint of a cholesterol-level lowering effect, flavor, appearance, storage stability at low temperatures, and industrial productivity of the fat or oil. When the derivative such as an ester is contained as ingredient (C), the content of ingredient (C) corresponds to an amount of the derivative in terms of a free phytosterol.

In the aspect of the present invention, the phytosterols (C) embrace phytostanols. Examples of the phytosterol include free phytosterols such as brassicasterol, isofucosterol, stigmasterol, 7-stigmasterol, α-sitosterol, β-sitosterol, campesterol, brassicastanol, isofucostanol, stigmastanol, 7-stigmastanol, α-sitostanol, β-sitostanol, campestanol, cycloartenol, cholesterol, and avenasterol, and esters such as fatty acid esters of these phytosterols, ferulate esters and cinnamate esters. Of these phytosterols, brassicasterol, campesterol, stigmasterol, and β-sitosterol are preferred from the standpoint of the industrial productivity of the fat or oil and flavor.

In the aspect of the present invention, the total content of brassicasterol, campesterol, stigmasterol, and β-sitosterol in the phytosterols (C) is preferably 90% or more, more preferably from 92 to 100%, even more preferably from 94 to 99% from the standpoint of flavor, appearance, industrial productivity of the fat or oil, precipitation of crystals, storage stability at low temperatures, and physiological effects.

A brassicasterol content in the phytosterols (C) is preferably from 0.5 to 8%. It is more preferably from 1 to 7.5%, even more preferably from 3 to 7% from the standpoint of flavor, appearance, industrial productivity of the fat or oil, precipitation of crystals, storage stability at low temperatures, and physiological effects.

A campesterol content in the phytosterols (C) is preferably from 10 to 40%. It is more preferably from 15 to 35%, even more preferably from 22 to 30% from the standpoint of flavor, appearance, industrial productivity of the fat or oil, precipitation of crystals, storage stability at low temperatures, and physiological effects.

A stigmasterol content in the phytosterols (C) is preferably from 3 to 30%. It is more preferably from 5 to 25%, even more preferably from 7 to 15% from the standpoint of flavor, appearance, industrial productivity of the fat or oil, precipitation of crystals, storage stability at low temperatures, and physiological effects.

A β-sitosterol content in the phytosterols (C) is preferably from 30 to 60%. It is more preferably from 35 to 58%, even more preferably from 40 to 56% from the standpoint of flavor, appearance, industrial productivity of the fat or oil, precipitation of crystals, storage stability at low temperatures, and physiological effects.

A cholesterol content in the phytosterols (C) is preferably 1% or less. It is more preferably from 0.01 to 0.8%, even more preferably from 0.1 to 0.7%, even more preferably from 0.2 to 0.6% from the viewpoint of reduction of a blood cholesterol level and industrial productivity of the fat or oil.

In the aspect of the present invention, when a fatty acid ester of a phytosterol is contained in the phytosterols (C), the unsaturated fatty acid content in the constituent fatty acids is preferably 80% or more. It is more preferably from 85 to 100%, even more preferably from 86 to 98%, even more preferably from 88 to 93% from the viewpoint of flavor, appearance, storage stability at low temperatures, precipitation of crystals, industrial productivity of the fat or oil, oxidation stability, and physiological effects.

In the aspect of the present invention, the weight ratio (CLA/PS) of a CLA content in DAG to the content of phytosterols (which may hereinafter be called "PS", simply) in the fat or oil is preferably less than 700. It is more preferably from 1 to 400, even more preferably from 5 to 250, even more preferably from 10 to 100, even more preferably from 15 to 70 from the standpoint of storage stability at low temperatures.

The above weight ratio is preferably applied to the case where a 1,3-DAG/1,2-DAG weight ratio in the fat or oil is from 1.5 to 3.8. It is more preferably applied to the case where the 1,3-DAG/1,2-DAG weight ratio in the fat or oil is from 2 to 3.5 and even more preferably applied to the case where the 1,3-DAG/1,2-DAG weight ratio in the fat or oil is from 2.1 to 3.2 from the standpoint of the storage stability at low temperatures, physiological effects, and industrial productivity of the fat or oil. When a derivative such as a fatty acid ester of a phytosterol (which may hereinafter be called "PSE", simply) is contained as the phytosterols, the CLA/PS weight ratio is determined using, as "PS", the total weight including the weight of the derivative converted into that of the free phytosterol.

In the aspect of the present invention, the fat or oil composition preferably contains a crystallization inhibitor (D) further. Examples of the crystallization inhibitor include polyol fatty acid esters such as polyglycerin condensed ricinoleate, polyglycerin fatty acid esters, sucrose fatty acid esters, sorbitan fatty acid esters, polyoxyethylene sorbitan fatty acid esters, and propylene glycol fatty acid esters, of which polyglycerin fatty acid esters, sucrose fatty acid esters and sorbitan fatty acid esters are preferred and polyglycerin fatty acid esters are even more preferred. The polyol fatty acid esters have preferably an HLB value of 4 or less, more preferably from about 0.1 to 3.5 as measured by the Griffin's calculation formula (*J. Soc. Cosmet. Chem.* 1, 311 (1949)).

In the aspect of the present invention, when the polyglycerin fatty acid ester is incorporated in the fat or oil composition as the crystallization inhibitor (D), the content of unsaturated fatty acids in the fatty acids constituting the polyglyerin fatty acid ester is preferably from 50 to 95%. It is more preferably from 51 to 80%, even more preferably from 52 to 60% from the standpoint of crystallization inhibition, solubility in the fat or oil, and oxidation stability. In addition, the content of unsaturated fatty acids is preferably adjusted to 50% or more in order to facilitate dissolution of the polyglycerin fatty acid ester in the fat or oil. Moreover, the content of the unsaturated fatty acids is preferably adjusted to 95% or less in order to inhibit the crystallization of the fat or oil. The unsaturated fatty acids constituting the polyglycerin fatty acid ester have preferably from 10 to 24 carbon atoms, more preferably from 16 to 22 carbon atoms. Specific examples of such an unsaturated fatty acid include palmitoleic acid, oleic acid, petroselic acid, elaidic acid, linoleic acid, linolenic acid, gadoleic acid, and erucic acid. Of these, oleic acid, linoleic acid, and gadoleic acid are preferred. The oleic acid content in the unsaturated fatty acids constituting the polyglycerin fatty acid ester is preferably 80% or more. It is more preferably from 90 to 99.8% from the standpoint of crystallization inhibition, solubility in the fat or oil, cost, oxidation stability, and flavor. The linoleic acid content in the unsaturated fatty acids constituting the polyglycerin fatty acid ester is preferably 10% or less. It is more preferably from 0.1 to 5% from the standpoint of crystallization inhibition, solubility in the fat or oil, cost, oxidation stability and flavor. A gadoleic acid content in the unsaturated fatty acids constituting the polyglycerin fatty acid ester is preferably 10% or less. It is more preferably from 0.1 to 5% from the standpoint of crystallization inhibition, solubility in the fat or oil, cost, oxidation stability, and flavor.

In the aspect of the present invention, when the polyglycerin fatty acid ester is incorporated in the fat or oil composition as the crystallization inhibitor (D), the saturated fatty acid content in the fatty acids constituting the polyglycerin fatty acid ester is preferably from 5 to 50%. It is more preferably from 20 to 49%, even more preferably from 40 to 48% from the standpoint of crystallization inhibition, solubility in the fat or oil, and oxidation stability. Such saturated fatty acids have preferably from 10 to 24 carbon atoms, more preferably from 12 to 22 carbon atoms. Specific examples include lauric acid, myristic acid, palmitic acid, stearic acid, arachidic acid, and behenic acid. Of these, myristic acid, palmitic acid, and stearic acid are preferred. A palmitic acid content in the saturated fatty acids constituting the polyglycerin fatty acid ester is preferably 80% or more. It is more preferably from 90 to 99.8% from the standpoint of crystallization inhibition, solubility in the fat or oil, cost, oxidation stability, and flavor. A myristic acid content in the saturated fatty acids constituting the polyglycerin fatty acid ester is preferably 10% or less. It is more preferably from 0.1 to 5% from the standpoint of crystallization inhibition, solubility in the fat or oil, cost, oxidation stability, and flavor. A stearic acid content in the saturated fatty acids constituting the polyglycerin fatty acid ester is preferably 10% or less. It is more preferably from 0.1 to 5% from the standpoint of crystallization inhibition, solubility in the fat or oil, cost, oxidation stability, and flavor.

In the aspect of the present invention, the content of the crystallization inhibitor (D) is, based on 100 parts of the fat or oil (A), preferably from 0.01 to 2 parts, more preferably from 0.02 to 0.5 part, even more preferably from 0.05 to 0.2 part from the standpoint of solubility in the fat or oil, cost, flavor, and crystallization inhibition.

In the aspect of the present invention, the fat or oil composition preferably contains an organic carboxylic acid having from 2 to 8 carbon atoms and/or a salt thereof further. The content of the organic carboxylic acid having from 2 to 8 carbon atoms is preferably from 0.001 to 0.01 part based on 100 parts of the fat or oil (A). It is more preferably from 0.0012 to 0.007 part, even more preferably from 0.0015 to 0.0045 part, even more preferably from 0.0025 to 0.0034 part from the standpoint of flavor, appearance, and oxidation stability. The organic carboxylic acid is preferably citric acid.

In the aspect of the present invention, the fat or oil composition of the present invention can be obtained by selecting the raw material fat or oil and preparation process so as to prepare the ingredient (A) having the composition falling within the predetermined range, adding the ingredient (B), adding the ingredient (C), the ingredient (D), the antioxidant, the organic carboxylic acid and/or salt thereof if necessary, heating the resulting mixture as needed, and stirring.

The fat or oil composition of the present invention can be applied to various foods because it is excellent in storage stability, flavor, texture, appearance, comfortable cooking work, and physiological effects.

Foods to which the fat or oil composition of the present invention can be applied include processed foods containing a fat or oil composition as a portion thereof. Examples of such fat or oil-containing processed foods include health foods, functional foods, and specific health foods which exhibit specific functions to achieve the promotion of health. Specific products include bakery foods such as breads, cakes, biscuits, pies, pizza crusts, and bakery mixes; oil-in-water emulsions such as soups, sauces, dressings, mayonnaises, coffee whiteners, ice creams, and whipped creams; water-in-oil emulsions such as margarines, spreads, and butter creams; snacks such as potato chips; confectioneries such as chocolates, caramels, candies, and desserts; processed meat foods such as hams, sausages, and hamburger steaks; milk products such as milk, cheeses, and yogurts; dough; enrober oils or fats; filling oils or fats; noodles; frozen foods; retort foods; drinks; and roux. These fat or oil-containing processed foods can each be produced by adding, in addition to the fat or oil composition of the present invention, food materials which are commonly employed, depending on the kind of the fat or oil-containing processed food. The fat or oil composition of the present invention may preferably be added generally in an amount of from 0.1 to 100%, more preferably from 1 to 80%, though depending on the kind of food.

The fat or oil composition of the present invention can be used as a food material such as a cooking oil for deep-fried foods and pan-fried foods. It is particularly suited for cooking or otherwise preparing delicatessens such as croquettes, tempura, fried pork cutlets, fried foods fried after seasoning, fried fish, and egg rolls; snacks such as potato chips, tortilla chips, and fabricated potatoes; fried confectioneries such as fried rice crackers; fried potatoes; fried chicken; donuts; instant noodles; and the like.

In producing a food by using the fat or oil composition of the present invention, when a fat or oil derived from the raw material of the food is contained, the weight ratio of the fat or oil derived from the food raw material to the fat or oil composition of the present invention, that is, a fat or oil derived from the food raw material/the fat or oil composition of the present invention ranges preferably from 95/5 to 1/99, more preferably from 95/5 to 5/95, even more preferably from 85/15 to 5/95, even more preferably from 40/60 to 5/95.

The fat or oil composition of the present invention may be used in an oil-in-water emulsion. The weight ratio of the oil phase to the water phase, that is, an oil phase/water phase water ratio ranges preferably from 1/99 to 90/10, more preferably from 10/90 to 80/20, even more preferably from 30/70 to 75/25. When the fat or oil composition of the present invention is used in an oil-in-water emulsion, an emulsifier is added in an amount of preferably from about 0.01 to 5%, even more preferably from 0.05 to 3%. Examples of the emulsifier include various proteins such as egg proteins, soybean proteins, milk proteins, proteins isolated from these proteins, and (partial) hydrolysates of these proteins; sucrose fatty acid esters; sorbitan fatty acid esters; polyoxyethylene sorbitan fatty acid esters; glycerin fatty acid monoesters; polyglycerin fatty acid esters; polyglycerine condensed ricinoleate; glycerin organic acid fatty acid esters; propylene glycol fatty acid esters; and lecithin and enzymatic hydrolysates thereof. When the fat or oil composition of the present invention is used in an oil-in-water emulsion, a stabilizer is contained preferably in an amount of from 0 to 5%, more preferably from about 0.01 to 2%. Examples of the stabilizer include thickening polysaccharides and starches, such as xanthan gum, gellan gum, guar gum, carageenan, pectin, tragacanth gum, and glucomannan (konjak mannan). It is also possible to use one or more flavor-imparting substances such as salt, sugar, vinegar, fruit juices, and seasonings; fragrance additives such as spices and flavors; coloring agents, preservatives, and antioxidants; and the like. Using these raw materials, fat or oil-containing oil-in-water type foods such as mayonnaises, dressings, coffee creams whiteners, ice creams, whipped creams and drinks can be prepared in the conventional manner.

The fat or oil composition of the present invention can also be used in a water-in-oil emulsion. The weight ratio of the water phase to the oil phase, that is, a water phase/oil phase weight ratio ranges preferably from 85/15 to 1/99, even more preferably from 80/20 to 10/90, even more preferably from 70/30 to 35/65. When the fat or oil composition of the present invention is used in a water-in-oil emulsion, an emulsifier is contained preferably in an amount of from 0.01 to 5%, more preferably from 0.05 to 30. Examples of the emulsifier include various proteins such as egg proteins, soybean proteins, milk proteins, proteins isolated from these proteins, and (partial) hydrolysates of these proteins; sucrose fatty acid esters; sorbitan fatty acid esters; polyoxyethylene sorbitan fatty acid esters; glycerin fatty acid monoesters; polyglycerin fatty acid esters; polyglycerine condensed ricinoleate; glycerin organic acid fatty acid esters; propylene glycol fatty acid esters; and lecithin and enzymatic hydrolysates thereof. It is also possible to use one or more flavor-imparting substances such as salt, sugar, vinegar, fruit juices, and seasonings; fragrance additives such as spices and flavors; stabilizers such as thickening polysaccharides and starches; coloring agents, preservatives; and the like. Using these raw materials, fat or oil-containing water-in-oil type foods such as margarines, spreads, and butter creams can be prepared in the conventional manner.

The fat or oil composition of the present invention has excellent physiological activities such as body fat accumulation inhibitory action, visceral fat accumulation inhibitory action, body weight increase inhibitory action, serum triglyceride rise inhibitory action, insulin resistance improving action, blood sugar level increase inhibitory action, HOMA index improving action, and food intake suppressive action. Owing to such excellent properties, the fat or oil composition of the present invention may be used for foods for specified health use, foods for patients, health function appeal foods, or pharmaceuticals.

The fat or oil composition of the present invention can be used for pharmaceuticals in the form of capsules, tablets, granules, powders, liquids or gels. Such pharmaceuticals can be prepared by adding, in addition to the fat or oil composition, an excipient, disintegrator, binder, lubricant, surfactant, alcohol, water, water-soluble polymer, sweetener, taste corrigent and acidulant, each ordinarily employed according to the dosage form. The amount of the fat or oil composition of the present invention to be added to a pharmaceutical is preferably from 0.1 to 80%, more preferably from 0.2 to 50%, even more preferably from 0.5 to 30%, though it may vary according to its purpose or dosage form. As a dose, the amount of from 0.2 to 50 g, in terms of the fat or oil composition, is preferably administered once or in several portions a day. Administration term is preferably at least 1 month, at least 2 months, or from 3 to 12 months.

The fat or oil composition of the present invention can be used for feeds. Examples of the feeds include livestock feeds for cows, pigs, chickens, sheep, horses, goats and the like; small animal feeds for rabbits, rats, mice and the like; fish or shellfish feeds for eels, red breams, young yellowtails, shrimps and the like; and pet foods for dogs, cats, birds, squirrels and the like. The amount of the fat or oil composition of the present invention to be added to a feed is usually from 1 to 30%, preferably from 1 to 20%, though depending on the purpose of the feed. The fat or oil composition of the present invention may be added by substituting it for a portion or all of the fat or oil in the feed.

Such a feed is prepared by mixing the above-described fat or oil composition with raw materials ordinarily used for feeds such as meats, proteins, grains, brans, lees, saccharides, vegetables, vitamins, and minerals as needed. Examples of meat include livestock or animal meat such as beef, pork, sheet meat (mutton or lamb), rabbit meat, and kangaroo meat and byproducts thereof; processed products (products obtained by rendering the above-exemplified raw materials such as meat balls, meat bone meals and chicken meal; and fish meat such as bluefin tuna, bonito, horse mackerel, sardine, scallop, turban shell and fish meal. Examples of the proteins include animal proteins, e.g., milk proteins such as casein and whey and egg proteins, and vegetable proteins such as soybean protein; those of the grains include wheat, barley, rye, milo, and corn; those of the brans include rice bran and wheat bran, and those of the lees include soybean lees. The total content of the meat, proteins, grains, brans, and lees in the feed is preferably from 5 to 93.9%.

Examples of the saccharides include glucose, oligosaccharide, sugar, molasses, starch, and liquid sugar and their content in the feed is preferably from 5 to 80%. As the vegetables, vegetable extracts and the like are usable and their content in the feed is preferably from 1 to 30%. Examples of the vitamins include A, $B_1$, $B_2$, D, E, niacin, pantothenic acid and carotene and their content in the feed is preferably from 0.05 to 10%. Examples of the minerals include calcium, phosphorus, sodium, potassium, iron, magnesium and zinc and their content in the feed is preferably from 0.05 to 10 wt %. In addition, the feed may contain additives ordinarily employed therefore such as gelling agent, shape retainer, pH regulator, seasoning, antiseptic, and nutrition supplement.

EXAMPLES

Example 1

Preparation of Fat or Oil (1) Preparation of Conjugated Linoleic Acid (CLA)

A mixture obtained by mixing 1050 g of propylene glycol with 350 g of potassium hydroxide was heated to 60° C. while stirring to completely dissolve potassium hydroxide. Nitrogen bubbling was then performed at 60° C. for 30 minutes to remove dissolved oxygen. The residue was then heated to 130° C. and 700 g of linoleic acid (product of Tokyo Chemical Industry) was added in portions. Under a nitrogen gas atmosphere, the resulting mixture was heated to 157° C. and stirred for 4 hours to effect a conjugation reaction. After cooling to room temperature, the reaction product was adjusted to pH 3 with 1 L of 5N hydrochloric acid. Solvent extraction was then performed with hexane. The solvent was distilled off by using an evaporator to obtain 700 g of CLA.

(2) Preparation of Fat or Oil A

A mixture obtained by mixing 1100 parts of CLA prepared in (1) with 110 parts of immobilized lipase was heated to 40° C. under a nitrogen atmosphere. To the resulting mixture was added 180.5 parts of glycerin and an esterification reaction was performed at 40° C. for 7 hours under reduced pressure (from 2 to 5 torr). After removal of the immobilized enzyme by filtration, the reaction product (containing 5.7% of TAG, 73.2% of DAG, 12.8% of MAG, and 8.3% of FFA) was charged in a silica gel column chromatography ("Wako C-200", product of Wako pure Chemical Industries) and eluted with an organic solvent to purify the reaction product. Described specifically, the reaction product was eluted successively with hexane, hexane-ethyl acetate (97:3, V/V), hexane-ethyl acetate (9:1, V/V), hexane-ethyl acetate (4:1, V/V), hexane-ethyl acetate (3:1, V/V), and hexane-ethyl acetate (2.5:1, V/V) to yield a DG fraction. A mixture obtained by adding 0.02 part of a tocopherol ("Mixed tocopherol MDE-6000", product of Yashiro) to 100 parts of the fat or oil obtained by distilling off the solvent by an evaporator was designated as Fat or oil A. The glyceride composition and fatty acid composition of Fat or oil A are shown in Table 1. Fat or oil A had a 1,3-DAG content of 78.7% and a 1,2-DAG content of 19.7%. A 1,3-DAG/1,2-DAG ratio (weight ratio) was therefore 4.

(3) Preparation of Fat or Oil B

A mixture obtained by mixing 520 parts of CLA prepared in (1) with 52 parts of immobilized lipase was heated to 40° C. under a nitrogen atmosphere. To the resulting mixture was added 56.9 parts of glycerin and an esterification reaction was performed at 50° C. for 20 hours under reduced pressure (from 2 to 5 torr). After removal of the immobilized enzyme by filtration, the reaction product (containing 41.8% of TAG, 36.8% of DAG, 1.2% of MAG, and 20.2% of FFA) was charged in silica gel column chromatography ("Wako C-200", product of Wako Pure Chemical Industries) and eluted with an organic solvent (hexane-ethyl acetate (97:3, V/V)) to remove the DG fraction and MG fraction. The residue was purified by subjecting it to florisil column chromatography further. Described specifically, after elution of the TG fraction with hexane and hexane-ethyl acetate (30:1, V/V), the solvent was distilled off by an evaporator. A mixture obtained by adding 0.02 part of a tocopherol ("Mixed tocopherol MDE-6000", product of Yashiro) to 100 parts by weight of the resulting fat or oil was designated as Fat or oil B. The glyceride composition and fatty acid composition of Fat or oil B are shown in Table 1.

(4) Preparation of Fat or Oil C

A mixture obtained by mixing 400 parts of a fish oil (product of Kao Corporation) with 16 parts of glycerin was subjected to an ester exchange reaction at 100° C. for 4 hours under reduced pressure (0.133 kPa) in the presence of 1.2 parts of sodium methylate. The reaction product thus obtained was purified by similar silica gel chromatography to that employed in (2) and the solvent was distilled off by an evaporator. To 100 parts of the fat or oil thus obtained was added 0.02 part of a tocopherol ("Mixed tocopherol MDE-6000", product of Yashiro) to obtain Fat or oil C. The glyceride composition and fatty acid composition of Fat or oil C are shown in Table 1.

(5) Preparation of Fat or Oil D

A mixture obtained by mixing 400 g of medium-chain fatty acid triglyceride ("Coconade MT", product of Kao Corporation) with 16 parts of glycerin was subjected to an ester exchange reaction at 100° C. for 4 hours under reduced pressure (0.133 kPa) in the presence of 1.2 parts of sodium methylate. The reaction product thus obtained was purified by similar silica gel chromatography to that employed in (2), followed by distillation of the solvent by an evaporator. To 100 parts of the fat or oil thus obtained was added 0.02 part of a tocopherol ("Mixed tocopherol MDE-6000", product of Yashiro) to obtain Fat or oil D. The glyceride composition and fatty acid composition of Fat or oil D are shown in Table 1.

(6) Preparation of Fat or Oil E

After 75 parts of potassium hydroxide was dissolved completely in 225 parts of propylene glycol and nitrogen bubbling was performed for 20 minutes, the resulting solution was heated to 120° C. under a nitrogen atmosphere. Then, 180 parts of safflower oil was added dropwise and a reaction was effected at 170° C. for 2.5 hours. The resulting reaction product (300 parts) and 12 parts of glycerin were subjected to an ester exchange reaction in the presence of 0.8 part of sodium methylate at 100° C. for 4 hours under reduced pressure (0.133 kPa). As in (2), the reaction product was fractionated by silica gel chromatography and the solvent was distilled off by an evaporator. To 100 parts of the fat or oil obtained by mixing the fractions was added 0.02 part of a tocopherol ("Mixed tocopherol MDE-6000", product of Yashiro) to yield Fat or oil E. The glyceride composition and fatty acid composition of the resulting fat or oil are shown in Table 1. A 1,3-DAG/1,2-DAG ratio (weight ratio) of Fat or oil E was 2.

(7) Preparation of Fat or Oil F

To 100 parts of a fat or oil obtained by mixing Fat or oil E and a rapeseed oil at a weight ratio of 1:2 were added 0.02 part of a tocopherol ("Mix tocopherol", product of Yashiro) and 4 parts of a phytosterol fatty acid ester ("CardioAid-S, product of ADM) to yield Fat or oil F. The glyceride composition and fatty acid composition of Fat or oil F are shown in Table 1. The constituent fatty acid composition of the rapeseed oil is shown in the footnote (*2) of Table 1.

(8) Preparation of Fat or Oil G and Fat or Oil H

Soybean oil fatty acid (455 parts) having a saturated fatty acid content reduced by wintering, 195 parts of rapeseed oil fatty acid, and 107 parts of glycerin were subjected to an esterification reaction with immobilized lipase ("Lipozyme RM IM", product of Novozymes) (40° C., 5 hours, 0.07 hPa). The immobilized lipase was filtered off and the residue was subjected to thin-film distillation, followed by washing with water and deodorization. To 100 parts of the resulting fat or oil was added 0.02 part of a tocopherol ("Mix tocopherol MDE-6000", product of Yashiro). To the resulting mixture were added 0.3 part and 4 parts of a phytosterol ("Phytosterol F", product of Tama Biochemical Co., Ltd.) to obtain Fat or oil G and Fat or oil H, respectively. The glyceride composition and fatty acid composition of Fat or oil G are shown in Table 1. Fat or oil G had a 1,3-DAG content of 57.7% and a 1,2-DAG content of 27.5%. A 1,3-DAG/1,2-DAG ratio (weight ratio) was therefore 2.

(9) Preparation of Fats or Oils I, J, K and Fats or Oils L, M, and N

Fat or oil A and Fat or oil G were mixed at weight ratios of 7:3, 5:5, and 3:7 to obtain Fat or oil I, Fat or oil J, and Fat or oil K, respectively. Fat or oil A and Fat or oil H were mixed at weight ratios of 7:3, 5:5, and 3:7 to obtain Fat or oil L, Fat or oil M, and Fat or oil N, respectively.

(10) Preparation of Fat or Oil O and Fat or Oil P

A rapeseed oil, Fat or oil A, and Fat or oil G were mixed at a weight ratio of 50:25:25 to obtain Fat or oil O. A rapeseed oil, Fat or oil A, and Fat or oil H were mixed at a weight ratio of 50:25:25 to obtain Fat or oil P. The rapeseed oil was similar to that employed for the preparation of Fat or oil F.

[Analysis Method]

(i) Distribution of Glyceride

A sample (10 mg) and 0.5 mL of a trimethylsilylating agent ("Silylating agent TH", product of Kanto Chemical Co., Inc.) were charged in a sample bottle made of glass. The bottle was sealed hermetically and then, heated at 70° C. for 15 minutes. Water (1 ml) and 2 mL of hexane were charged successively in the bottle, followed by vigorous shaking. After allowing to stand, a hexane phase was extracted and subjected to gas chromatography (GLC) to analyze its glyceride distribution.

GLC Conditions:

Apparatus: "6890 model" product of Hewlett Packard
Column: DB-1HT (product of J&W Scientific) 7 m
Column temperature: initial=80° C., final=340° C. Heating rate=10° C./min., kept at 340° C. for 20 min.
Detector: FID, temperature=350° C.
Injection part:split ratio=50:1, temperature=320° C.
Sample injection amount: 1 μL
Carrier gas: helium, flow rate=1.0 mL/min.

(ii) Constituent Fatty Acid Composition

To about 12 mg of a sample was added 0.6 mL of a 1/2N sodium hydroxide/methanol solution. After addition of 0.6 mL of a boron trifluoride/methanol complex methanol solution (product of Wako Pure Chemical Industries), the resulting mixture was heated at 70° C. for 30 minutes. Saturated brine (1 mL) and 1 mL of hexane were added successively, followed by thorough shaking. A hexane phase was extracted and anhydrous sodium sulfate was added to prepare a methyl ester of the fatty acid.

The methyl ester of the fatty acid thus obtained was analyzed by GLC.

GLC Conditions:

Apparatus: "6890 model" product of Hewlett Packard
Column: "CP-Sil88 for Frame" (product of GL Sciences Inc.) 0.25 mm×50 m
Column temperature: initial=150° C., final=225° C.
  The column temperature was kept at 150° C. for 5 minutes, heated at a rate of 2° C./min, and then, kept at 225° C. for 15 minutes.
Detector: FID, temperature=250° C.
Injection part:split ratio=40:1, temperature=250° C.
Sample injection amount: 1 μL
Carrier gas: helium, flow rate=1.0 mL/min.

c: The fat or oil is poor because it emits both an odor due to deterioration and a chemical odor.

d: The fat or oil is very poor because it emits a strong odor due to deterioration and a chemical odor.

Appearance a: The fat or oil is very good because it is in liquid form similar to a typical oil (salad oil).

b: The fat or oil is good because it is slightly more viscous than the typical oil.

c: The fat or oil is poor because it is partially in gel form.

d: The fat or oil is very poor because a major part of it is in gel form.

TABLE 1

|  | Fat or oil A | Fat or oil B | Fat or oil C | Fat or oil D | Fat or oil E | Fat or oil F*1 | Fat or oil G |
|---|---|---|---|---|---|---|---|
| Glyceride composition wt. % | | | | | | | |
| TAG | 1.3 | 98.3 | 1.9 | 0 | 35.4 | 78.3 | 14.3 |
| DAG | 98.4 | 1.3 | 98.0 | 97.6 | 62.9 | 21.0 | 85.2 |
| MAG | 0 | 0 | 0 | 2.2 | 1.5 | 0.5 | 0.5 |
| FFA | 0.3 | 0.4 | 0.1 | 0.2 | 0.2 | 0.2 | 0.1 |
| Composition of all the fatty acids wt. % | | | | | | | |
| C8:0 | n.d. | n.d. | n.d. | 85.3 | n.d. | n.d. | n.d. |
| C10:0 | n.d. | n.d. | n.d. | 14.7 | n.d. | n.d. | n.d. |
| C12:0 | n.d. | n.d. | n.d. | n.d. | n.d. | n.d. | n.d. |
| C14:0 | n.d. | n.d. | 4.3 | n.d. | n.d. | n.d. | n.d. |
| C16:0 | n.d. | n.d. | 14.6 | n.d. | 6.9 | 5.1 | 3.1 |
| C16:1 | n.d. | n.d. | 6.8 | n.d. | n.d. | n.d. | n.d. |
| C18:0 | n.d. | n.d. | 3.8 | n.d. | 2.7 | 2.2 | 1.3 |
| C18:1 | 5.2 | 5.2 | 16.6 | n.d. | 12.5 | 44.8 | 38.3 |
| C18:2 | | | | | | | |
| CLA | 90.4 | 90.4 | n.d. | n.d. | 73.8 | 24.6 | n.d. |
| Other than CLA | n.d. | n.d. | 2.8 | n.d. | 3.6 | 15.4 | 48.6 |
| C18:3 | n.d. | n.d. | n.d. | n.d. | 0.1 | 6.5 | 7.9 |
| C20:1 | n.d. | n.d. | 6.6 | n.d. | n.d. | 0.5 | 0.6 |
| C20:5 | n.d. | n.d. | 8.7 | n.d. | n.d. | n.d. | n.d. |
| C22:6 | n.d. | n.d. | 9.4 | n.d. | n.d. | n.d. | n.d. |
| CLA(DAG)/CLA(TAG) weight ratio | 1 | 1 | 1 | 1 | 1 | 6.6 | — | n.d.: not detected
*1 A 1:2 (weight ratio) mixture of Fat or oil E and rapeseed oil*2
*2: Composition of fatty acids constituting the rapeseed oil (C16:0 = 4.2%, C18:0 = 2%, C18:1 = 61%, C18:2 (CLA) = 0%, C18:2 (other than CLA) = 21.3%, C18:3 = 9.7%)

The fatty acid composition in each fat or oil shown in Table 1 was regarded similar to the composition of all the fatty acids in respective glycerides with the exception of Fat or oil F.

Example 2

Storage Test

Storage test was performed in the following manner by using Fat or oil A and Fat or oil B. Each of the oils or fats (20 g) was placed in a sample bottle (having a capacity of 50 ml) made of glass. After nitrogen sealing, the bottle was hermetically sealed and stored in a refrigerator of −20° C. Five years later, the bottle was allowed to stand at normal temperature to thaw the fat or oil. The bottle was opened and the odor and appearance of the fat or oil was organoleptically evaluated based on the following criteria. The results are shown in Table 2.

Odor:

a: The fat or oil is very good because it is almost free from an odor due to deterioration and a chemical odor.

b: The fat or oil is good because it is free from a chemical odor, though slightly emitting an odor due to deterioration.

TABLE 2

|  | Odor | Appearance |
|---|---|---|
| Fat or oil A (example invention product) | B | a |
| Fat or oil B (comparative product) | D | d |

The storage test has revealed that the example invention product is superior in odor and appearance to the comparative product, showing that the example invention product has good storage stability.

Example 3

Animal Experiment

A feed having the composition as shown in Table 3 was prepared in the conventional manner. Six to seven-week-old Zucker rats were divided into four groups, each group consisting of 6 rats. First, they were preliminarily reared for four days with Feed 1 (a predetermined feed amount). Then, they were reared for 9 days with each feed. The feed amount with each feed was measured every day. On the last feeding day, they were sacrificed. The liver, perinephric fat tissue, and epididymal fat tissue were excised therefrom and weighed. In addition, a triglyceride amount in the liver was measured. The results are shown in Table 4.

TABLE 3

| | Composition of feed (parts by weight) | | | |
|---|---|---|---|---|
| | Feed 1 | Feed 2 | Feed 3 | Feed 4 |
| Casein | 20 | 20 | 20 | 20 |
| Cellulose | 4 | 4 | 4 | 4 |
| Mineral mixture | 3.5 | 3.5 | 3.5 | 3.5 |
| Vitamin mixture | 1 | 1 | 1 | 1 |
| Potato starch | 61.5 | 57.5 | 57.5 | 57.5 |
| Fat or oil *[3] | W | X | Y | Z |
| Corn oil *[4] | 10 | 10 | 10 | 10 |
| Fat or oil A | 0 | 4 | 0 | 0 |
| Fat or oil C | 0 | 0 | 4 | 0 |
| Fat or oil D | 0 | 0 | 0 | 4 |

*[3] A corn oil was used as Fat or oil W, while mixtures of 10 parts of the corn oil with 4 parts of Fat or oil A, Fat or oil C, and Fat or oil D were used as Fat or oil X, Fat or oil Y, and Fat or oil Z, respectively.
*[4] Constituent fatty acid composition of the corn oil: (C16:0 = 13%, C18:0 = 2.5%, C18:1 = 30.5%, C18:2(CLA) = 0% C18:2 (other than CLA) = 52%, C18:3 = 1%)

TABLE 4

| | Feed 1 | Feed 2 | Feed 3 | Feed 4 |
|---|---|---|---|---|
| Liver triglyceride (mg/g-liver/100 g-weight) | 498 | 126 | 274 | 234 |
| Perinephric fat tissue (g/100 g-weight) | 0.88 | 0.70 | 0.80 | 0.84 |
| Epididymal fat tissue (g/100 g-weight) | 2.62 | 2.64 | 2.67 | 2.52 |
| Total ingestion amount (g/9 days) | 1550 | 1100 | 1500 | 1460 |

It has been elucidated that administration of the feed (Feed 2) containing the invention product reduces a triglyceride level in the liver and the amount of the perinephric fat tissue compared with administration of the comparative products (Feeds 1, 3 and 4). In addition, the results have revealed that the total ingestion amount shows a drastic decrease and the feed containing the invention product has a feed-intake suppressive effect.

Example 4

Storage Stability Test 1 at Low Temperatures

Mixtures obtained by adding, to Fat or oil A, with a phytosterol ("Phytosterol F", product of Tama Biochemical Co., Ltd.) in amounts of 1%, 2%, and 4% were used as Fat or oil Aa, Fat or oil Ab, and Fat or oil Ac, respectively. On the other hand, mixtures obtained by adding, to Fat or oil A, with a phytosterol fatty acid ester ("CardioAid-S, product of ADM) in amounts of 1%, 2% and 4% were used as Fat or oil Ad, Fat or oil Ae, and Fat or oil Af, respectively.

Each fat or oil (10 g) was charged in a 20-mL sample bottle made of glass. The bottle was sealed with a lid and allowed to stand in a temperature-controlled bath of 5° C. or 10° C. The conditions of the sample after 6 hours and 24 hours were observed visually based on the following evaluation criteria and evaluated. Evaluation results are shown in Table 5.
Score 4: The fat or oil is clear without precipitation or turbidity and has fluidity.
Score 3: The fat or oil has slight turbidity and precipitation, but has fluidity.
Score 2: The fat or oil has some precipitation and its fluidity is impaired.
Point 1: The fat or oil becomes solidified and has no fluidity.

TABLE 5

| | 10° C. | | 5° C. | |
|---|---|---|---|---|
| | 6 hrs | 24 hrs | 6 hrs | 24 hrs |
| Fat or oil A PS0% | 4 | 4 | 2 | 1 |
| Fat or oil Aa PS1% | 4 | 4 | 4 | 2 |
| Fat or oil Ab PS2% | 4 | 4 | 4 | 4 |
| Fat or oil Ac PS4% | 4 | 4 | 4 | 4 |
| Fat or oil Ad PSE1% | 4 | 4 | 4 | 1 |
| Fat or oil Ae PSE2% | 4 | 4 | 4 | 2 |
| Fat or oil Af PSE4% | 4 | 4 | 4 | 4 |

The results have revealed that by the incorporation of a phytosterol (PS) or a phytosterol fatty acid ester (PSE), storage stability of CLA-DAG at low temperatures is improved.

Example 5

Storage Stability Test 2 at Low Temperatures

Each of Oils or fats A, G, H, I-K, L-N, O and P (10 g) was charged in a 20-ml sample bottle made of glass. The bottle was sealed with a lid and allowed to stand in a temperature-controlled bath of 5° C. and 10° C. The conditions of each sample after 6 hours and after 24 hours were visually observed based on similar evaluation criteria to those employed in Example 4 and evaluation was performed. The evaluation results are shown in Table 6. In Table 1, a weight ratio of the CLA content in DAG to the PS content in the fat or oil (CLA/PS) was calculated assuming that a composition of all the fatty acids constituting Fat or oil A or Fat or oil G was similar to the composition of fatty acids constituting DAG.

TABLE 6

| | | 10° C. | | 5° C. | | CLA/PS |
|---|---|---|---|---|---|---|
| | | 6 hrs | 24 hrs | 6 hrs | 24 hrs | ratio |
| Fat or oil A | PS 0% | 4 | 4 | 2 | 1 | — |
| Fat or oil G | PS 0.3% | 4 | 4 | 4 | 4 | 0 |
| Fat or oil H | PS 4% | 4 | 4 | 4 | 4 | 0 |
| Fat or oil I | PS 0.09% | 4 | 4 | 2 | 1 | 703 |
| Fat or oil J | PS 0.15% | 4 | 4 | 4 | 4 | 301 |
| Fat or oil K | PS 0.21% | 4 | 4 | 4 | 4 | 129 |
| Fat or oil L | PS 1.2% | 4 | 4 | 4 | 4 | 52.8 |
| Fat or oil M | PS 2% | 4 | 4 | 4 | 4 | 22.6 |
| Fat or oil N | PS 2.8% | 4 | 4 | 4 | 4 | 9.7 |
| Fat or oil O | PS 0.325% | 4 | 4 | 4 | 4 | 69.5 |
| Fat or oil P | PS 1.25% | 4 | 4 | 4 | 4 | 18.1 |

The results have revealed that when the weight ratio (CLA/PS) of a CLA content in DAG to a PS content in the fat or oil is less than 700, the fat or oil has improved storage stability at low temperatures.

The invention claimed is:
1. A fat or oil composition with improved storage stability at low temperatures comprising the following ingredients (A), (B) and (C):
(A) 100 parts by weight of a fat or oil comprising:
15 wt. % or more of diacylglycerols having, in the constituent fatty acids thereof,
an unsaturated fatty acid content of 80 wt. % or more,
a conjugated linoleic acid ("CLA") content of from 5 to 92 wt. %, and
an ω3 unsaturated fatty acid content of less than 15 wt. %;

wherein the fat or oil has a monoacylglycerol content of 5 wt. % or less and a free fatty acid content of 5 wt. % or less; and wherein the fat or oil comprises 1,3-diacylglycerol/1,2-diacylglycerol at a weight ratio of from 1 to 5;

(B) from 0.001 to 2 parts by weight of a tocopherol; and (C) from 0.05 to 30 parts by weight of a phytosterol;

wherein the ratio of CLA to phytosterol ranges from 1 to 400.

2. A food comprising the fat or oil composition as claimed in claim 1.

3. A feed comprising the fat or oil composition as claimed in claim 1.

4. A pharmaceutical comprising the fat or oil composition as claimed in claim 1.

5. The fat or oil composition of claim 1, wherein (A) contains 15 to 70 wt % of conjugated linoleic acid.

6. A method for reducing triglyceride levels comprising administering to a subject in need thereof an effective amount of the fat or oil composition of claim 1.

7. A process for making the fat or oil composition of claim 1 comprising admixing linoleic acid with diacylglyerol and tocopherol to form said fat or oil composition.

8. A fat or oil composition with improved storage stability at low temperatures comprising the following ingredients (A), (B) and (C):

(A) 100 parts by weight of a fat or oil comprising 35 wt. % or more of diacylglycerols having, in the constituent fatty acids thereof, an unsaturated fatty acid content of 80 wt. % or more, a conjugated linoleic acid content of from 5 to 92 wt. % and an ω3 unsaturated fatty acid content of less than 15 wt. %; wherein the fat or oil has a monoacylglycerol content of 5 wt. % or less and a free fatty acid content of 5 wt. % or less; and wherein the fat or oil comprises 1,3-diacylglycerol/1,2-diacylglycerol at a weight ratio of from 1 to 5; and (B) from 0.001 to 2 parts by weight of a tocopherol; and (C) from 0.05 to 30 parts by weight of a phytosterol;

wherein the ratio of CLA to phytosterol ranges from 1 to 400.

9. A pharmaceutical comprising the fat or oil composition as claimed in claim 8.

10. A method for reducing triglyceride levels comprising administering to a subject in need thereof an effective amount of the fat or oil composition of claim 8.

11. A process for making the fat or oil composition of claim 8 comprising admixing linoleic acid with diacylglyerol and tocopherol to form said fat or oil composition.

12. A fat or oil composition with improved storage stability at low temperatures comprising the following ingredients (A), (B) and (C):

(A) 100 parts by weight of a fat or oil comprising 35 wt. % or more of diacylglycerols having, in the constituent fatty acids thereof, an unsaturated fatty acid content of 80 wt. % or more, a conjugated linoleic acid content ranging from 73.3 to 92 wt. % and an ω3 unsaturated fatty acid content ranging from 1 to 10 wt. %; wherein the fat or oil has a monoacylglycerol content of 5 wt. % or less and a free fatty acid content of 5 wt. % or less; and wherein the fat or oil comprises 1,3-diacylglycerol/1,2-diacylglycerol at a weight ratio of from 1 to 5; and (B) from 0.001 to 2 parts by weight of a tocopherol; and (C) from 0.05 to 30 parts by weight of a phytosterol;

wherein the ratio of CLA to phytosterol ranges from 1 to 400.

13. A pharmaceutical comprising the fat or oil composition as claimed in claim 12.

14. A method for reducing triglyceride levels comprising administering to a subject in need thereof an effective amount of the fat or oil composition of claim 12.

15. A process for making the fat or oil composition of claim 12 comprising admixing linoleic acid with diacylglyerol and tocopherol to form said fat or oil composition.

16. The fat or oil composition of claim 1, wherein the weight ratio of 1,3-diacylglycerol to 1,2-diacylglycerol ranges from 1.5 to 3.8.

17. The fat or oil composition of claim 8, wherein the weight ratio of 1,3-diacylglycerol to 1,2-diacylglycerol ranges from 1.5 to 3.8.

18. The fat or oil composition of claim 12, wherein the weight ratio of 1,3-diacylglycerol to 1,2-diacylglycerol ranges from 1.5 to 3.8.

19. The fat or oil composition of claim 1, wherein storage stability is determined at 5° C. or at 10° C.

20. The fat or oil composition of claim 8, wherein storage stability is determined at 5° C. or at 10° C.

21. The fat or oil composition of claim 12, wherein storage stability is determined at 5° C. or at 10° C.

* * * * *